US00PP22486P2

(12) United States Plant Patent
Korlipara

(10) Patent No.: US PP22,486 P2
(45) Date of Patent: Feb. 7, 2012

(54) ***COREOPSIS* PLANT NAMED 'PINEAPPLE PIE'**

(50) Latin Name: ***Coreopsis* spp.**
Varietal Denomination: Pineapple Pie

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,266

(22) Filed: Nov. 10, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Annette Para
(74) *Attorney, Agent, or Firm* — Klarquist Sparkman, LLP

(57) ABSTRACT

A new and distinct *Coreopsis* plant named 'Pineapple Pie' characterized by small daisy-type flowers that grow to 3 cm in diameter, flowers that are golden yellow with deep red eyes, grass green foliage on short stems, flowering for the whole summer, and a dense, mounding habit.

1 Drawing Sheet

Botanical denomination: *Coreopsis* spp.
Variety designation: 'Pineapple Pie'.
Parentage: *Coreopsis* 'Little Penny' (U.S. Plant Pat. No. 18,502)×*Coreopsis* 'Rum Punch' (U.S. Plant Pat. No. 18,889)
Cross reference to: parents above and co-pending applications for *Coreopsis* 'Pumpkin Pie' (U.S. Plant patent application No. 12/927,226), 'Cherry Pie' (U.S. Plant patent application No. 12/927,270).

BACKGROUND OF THE INVENTION

The present invention relates to a new and distinct *Coreopsis* and given the cultivar name 'Pineapple Pie'. *Coreopsis* is in the family *Asteraceae*. This new cultivar originated from a controlled cross of *Coreopsis* 'Rum Punch' (U.S. Plant Pat. No. 18,889) as the seed parent and *Coreopsis* 'Little Penny' (U.S. Plant Pat. No. 18,502) as the pollen parent. The breeding plan was to make a series like *Coreopsis* 'Little Penny'.

Compared to the seed parent, *Coreopsis* 'Little Penny', the new hybrid has flowers that are larger, and golden yellow with deep red eyes rather than copper with small yellow eyes. Compared to the pollen parent, *Coreopsis* 'Rum Punch', the new cultivar has smaller flowers that are golden yellow with deep red eyes rather than orangey-rose colored. The new cultivar has a smaller, tighter habit than *Coreopsis* 'Rum Punch'.

SUMMARY OF THE INVENTION

The following traits have been repeatedly observed and are determined to be the unique characteristics of the new variety. These characteristics in combination distinguish *Coreopsis* 'Pineapple Pie' as a new and distinct cultivar:

1. small daisy-type flowers that grow to 3 cm in diameter,
2. flowers that are golden yellow with deep red eyes,
3. grass green foliage on short sterns,
4. flowering for the whole summer, and
5. a dense, mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows one-year-old *Coreopsis* Pineapple Pie' growing in the ground in the trial field in August in Canby, Oreg.

DETAILED PLANT DESCRIPTION

The following is a detailed description of the new *Coreopsis* cultivar based on observations of a four-month-old specimen growing in a one gallon container in a cool greenhouse in Canby, Oregon. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type.*—Herbaceous perennial.
*Hardiness.*—USDA Zones 7 to 9.
*Size.*—19 cm wide and 21 cm tall to top of inflorescences.
*Form.*—Mound.
*Vigor.*—Excellent.
*Roots.*—Fibrous, stems root easily from stem cuttings.

Stem:

*Type.*—Ascending.
*Size.*—10 cm tall to where branches for flowering and 4 mm wide.
*Number of stems from the crown.*—1.
*Internode length.*—1 cm to 1.5 cm.
*Surface.*—Glabrous.
*Color.*—Yellow Green 137A.

Leaf:

*Type.*—Simple.

*Shape.*—Linear.

*Arrangement.*—Opposite.

*Size.*—Grows to 5 cm long and 5 mm wide.

*Margins.*—Entire.

*Petiole.*—Sessile.

*Apex.*—Acute.

*Base.*—Cuneate clasping.

*Surface texture.*—Glabrous on top and bottom sides.

*Venation.*—Pinnate.

*Color.*—Topside Yellow Green 137A, bottom side Yellow Green 147B.

Inflorescence:

*Type.*—Long stalked terminal heads of daisy type inflorescences, slightly cupped up.

*Peduncle.*—Grows to 9 cm long, 1 mm wide, glabrous, Green 137A.

*Size.*—Grows to 3 cm wide and 5 mm deep.

*Immature.*—Globular, 6 mm wide and 5 mm deep, Greyed Yellow 163B on the sides and Yellow 2A on top, glabrous.

*Receptacle.*—Disc shaped, 2 mm wide and 1 mm deep, Yellow Green 146B.

*Phyllary.*—In 2 series, first series closet to ray florets 3 mm deep and 8 mm wide, 8 in number, each 4 mm long and 2 mm wide, ovate, entire, acute, glabrous on both sides, both sides Greyed Orange 167A on top half and Yellow Green 146B on bottom half; lower series in an area 2 mm deep and 1.5 mm wide, 8 in number, 2 mm long and 1 mm wide, each ovate, entire, acute, both sides glabrous and Yellow Green 147A.

*Lastingness.*—Each inflorescence lasts about a week on the plant.

Florets:

*Type.*—Composite.

*Ray florets.*—8 in number with no pistil or stamen, grows to 15 mm long, 8 mm wide, obovate with the tip three-lobed with lobe tips obtuse and the central lobe the longest and sometimes notched, margins entire, glabrous on both sides; topside Yellow Orange 15A except at base where Greyed Purple 187B, bottom side Yellow Orange 15D except at base where Greyed Purple 187D.

*Disc.*—Conic, deeper with maturity, 6 mm wide and becoming 4 mm deep with maturity, Greyed Purple 187A before opening, after opening Yellow Orange 21 B with a background of Greyed Purple 187A.

*Disc florets.*—Tubular, with stamen and pistil, about 76 in number, 6 mm long and 1 mm wide, tubular; corolla 4 mm long, Greyed Purple N 186D on the 4 lobes to Yellow Orange 15A on the upper tube to Green Yellow IC; pistil 1, ovary 1 mm long, Green Yellow I C, style 4 mm long, extruding, with 2-branched stigma, stigma and style Yellow Orange 21 B; stamen 5, anthers 1.3 mm long, Greyed Purple187A, pollen Yellow 10A.

*Bloom period.*—June through September in Canby, Oreg.

*Fragrance.*—Light, Chrysanthemum-like.

*Seed.*—None seen.

*Fertility.*—Unknown.

Disease and pests: *Coreopsis* are susceptible to mildew and fungal spots. No resistance is known for this variety.

I claim:

1. A new and distinct *Coreopsis* plant as herein illustrated and described.

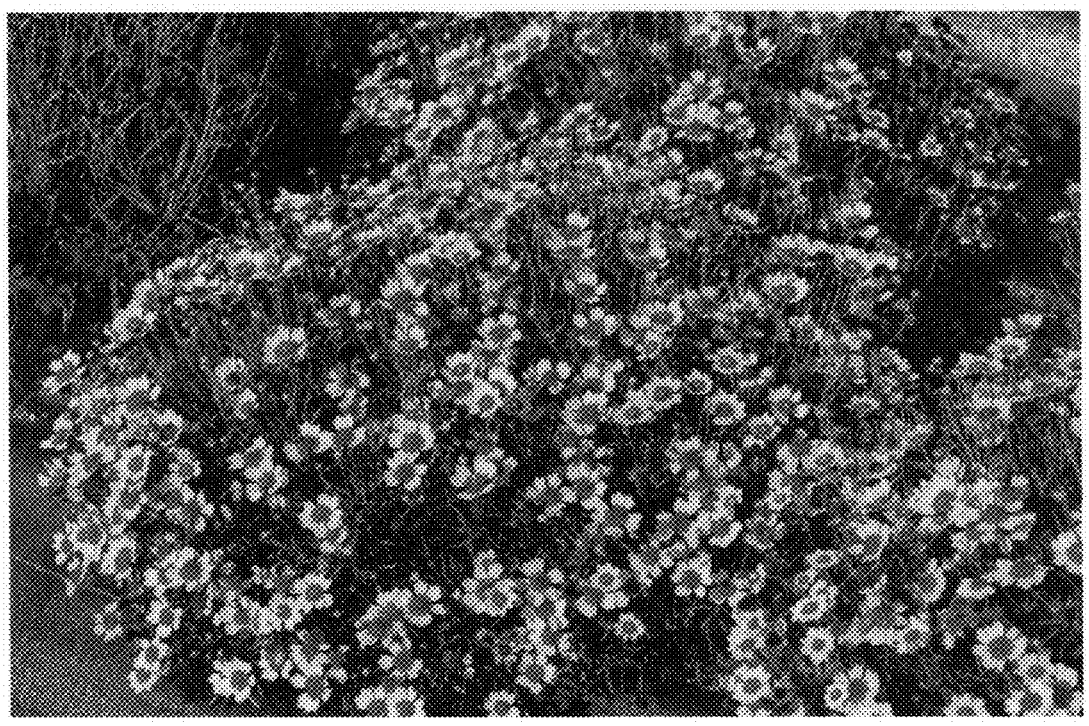

* * * * *